US00PP09701P

United States Patent [19]

VandenBerg

[11] Patent Number: Plant 9,701

[45] Date of Patent: Nov. 19, 1996

[54] CHRYSANTHEMUM PLANT NAMED 'PINK CINDERELLA'

[75] Inventor: Cornelis P. VandenBerg, Salinas, Calif.

[73] Assignee: Yoder Brothers, Inc., Barberton, Ohio

[21] Appl. No.: 525,315

[22] Filed: Sep. 7, 1995

[51] Int. Cl.[6] ..... A01H 5/00

[52] U.S. Cl. ..... Plt./80

[58] Field of Search ..... Plt./76, 80

[56] References Cited

U.S. PATENT DOCUMENTS 4,616,099 10/1986 Sparkes ..... 47/58

OTHER PUBLICATIONS

Broertjes, et al., 1980, "A mutant of a mutant of a . . . Irradiation of progressive radiation induced mutants in a mutation breeding programme with *Chrysanthemum morifolium*", Euphytica, 29:525–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X–rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in Chrysanthemum using x– and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Pink Cinderella particularly characterized by its flat capitulum form; decorative capitulum type; red-purple ray floret color; diameter across face of capitulum of 64 to 73 mm when fully opened, when grown as a single stem spray cut mum; flowering response in Salinas under normal temperatures is 47 to 54 days after start of short days; flowering response in Bogota, Colombia is 59 to 63 days; plant height is 86 to 94 cm when grown in Salinas with 14 to 18 long days prior to start of short days; height is 104 to 112 cm when grown in Bogota with 21 long days prior to start of short days; peduncle length of the first lateral at flowering after removing the apical bud without growth regulator applications is 8 to 13 cm when grown in Salinas, and 13 to 15 cm when grown in Bogota; peducle length of the fourth lateral at flowering is 10 to 15 cm when grown in Salinas, and 18 to 20 cm when grown in Bogota; high production of flowers per stem, with 10 to 14 laterals developing; top laterals produce one terminal flower, lower laterals produce one terminal flower and 2 to 4 secondary flowers; and excellent tolerance to low night temperatures for bud initiation and flower development.

1 Drawing Sheet

The present invention comprises a new and distinct cultivar of chrysanthemum, botanically known as *Dendranthema grandiflora,* and referred to by the cultivar name Pink Cinderella.

Pink Cinderella, identified as 0026 (90-985D01), is a product of a mutation induction program. The new cultivar was discovered and selected by inventor Cornelis P. VandenBerg on Mar. 26, 1993 in controlled environment in Salinas, Calif. as one flowering plant within a flowering block established as rooted cuttings from stock plants which had been exposed as unrooted cuttings to an X-ray source of 2000 rads in Fort Myers, Fla. on Sep. 24, 1992. The irradiated parent cultivar was the cultivar Cinderella, disclosed in U.S. Plant Pat. No. 8,936 and described as a decorative spray cut mum with a light pink ray floret color.

The irradiation program resulting in Pink Cinderella had as its primary objective the expansion of color ranges of the parent cultivar Cinderella. The irradiation program comprised irradiation of cuttings of the parent cultivar at irradiation levels of 1500, 1750 and 2000 rads. A total of 768 cuttings harvested from a total of 225 irradiated plants were planted on Jan. 18, 1993. Of these, 14 initial selections were made, which selections were then revegetated and reflowered. Three consecutive flowerings resulted in discarding 8 of the original 14 selections on Dec. 6, 1993. The remaining selections were maintained as PIs (Possible Introductions) and further trialed in Salinas, Calif. and Bogota, Colombia, ultimately resulting in discarding two of the remaining selections on Nov. 12, 1994 and the decision to introduce the 4 remaining selections as Pink Cinderella, White Cinderella, Peach Cinderella and Golden Cinderella, White Cinderella, Peach Cinderella and Golden Cinderella are disclosed in pending application Ser. Nos. 08/525,317; 8/525,312, and 08/525,313, respectively.

The first act of asexual reproduction of Pink Cinderella was accomplished when vegetative cuttings were taken from the initial selection in June of 1993 in a controlled environment in Salinas, Calif., by technicians working under supervision of Cornelis P. VandenBerg.

Horticultural examination of controlled flowerings of successive plantings has shown that the unique combination of characteristics as herein disclosed for Pink Cinderella are firmly fixed and are retained through successive generations of asexual reproduction.

Pink Cinderella has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Bogota, Colombia, under greenhouse conditions which approximate those generally used in commercial greenhouse practice. The low night temperature tolerance was determined in repeated flowerings in Bogota, Colombia, with an average minimum low night temperature inside the greenhouse during our trials ranging as low as 5 to 8 degrees Celsius.

The following traits have been repeatedly observed and are determined to be basic characteristics of Pink Cinderella, which, in combination, distinguish this Chrysanthemum as a new and distinct cultivar:

1. Flat capitulum form.
2. Decorative capitulum type.
3. Red-purple ray floret color.
4. Diameter across face of capitulum of 64 to 73 mm when fully opened, when grown as a single stem spray cut mum.
5. Flowering response in Salinas under normal temperatures is 47 to 54 days after start of short days. Flowering response in Bogota, Colombia is 59 to 63 days.
6. Plant height is 86 to 94 cm when grown in Salinas with 14 to 18 long days prior to start of short days; height is 104 to 112 cm when grown in Bogota with 21 long days prior to start of short days.
7. Peduncle length of the first lateral at flowering after removing the apical bud without growth regulator applications is 8 to 13 cm when grown in Salinas, and 13 to 15 cm when grown in Bogota. Peduncle length of the fourth lateral at flowering is 10 to 15 cm when grown in Salinas, and 18 to 20 cm when grown in Bogota.
8. High production of flowers per stem, with 10 to 14 laterals developing. Top laterals produce one terminal flower, lower laterals produce one terminal flower and 2 to 4 secondary flowers.
9. Excellent tolerance to low night temperatures for bud initiation and flower development.

The accompanying photographic drawing is a side view of a single stem cut spray mum of Pink Cinderella, with the colors being as nearly true as possible with illustrations of this type.

Of the commercial cultivars known to the inventor, the most similar in comparison to Pink Cinderella is the parent cultivar Cinderella. All traits of Pink Cinderella are similar to those of Cinderella, except for the ray floret color and the flowering response to short days. The ray floret color of Pink Cinderella is darker pink (RHS 62C to 65B) than the ray floret color of Cinderella (RHS 62D). flowering response of Pink Cinderella has been 1 to 2 days slower than the flowering response of Cinderella.

Comparing the sibling cultivars, White Cinderella, Pink Cinderella and Golden Cinderella differ from Cinderella and from each other with respect to ray floret color. In addition to color, Pink Cinderella differs from Cinderella, White Cinderella and Golden Cinderella by its 1–2 days slower flowering response. Peach Cinderella has a 1–4 days slower response than Cinderella, White Cinderella and Golden Cinderella, and has a 3–10 cm shorter plant height compared to Cinderella and all of the other siblings.

In the following description color references are made to the Royal Horticultural Society Colour Chart. The color values were determined on plant material grown as a single stem spray cut mum grown in Salinas, Calif. on Jun. 27, 1995.

Classification:

*Botanical.*—*Dendranthema grandiflora* cv Pink Cinderella.

*Commercial.*—Flat decorative spray cut mum.

INFLORESCENCE

A. Capitulum:
- *Form.*—Flat
- Type.—Decorative.
- Diameter across face.—64 to 73 mm when fully opened.

B. Corolla of ray florets:
- *Color (general tonality from a distance of three meters).*—Red-purple.
- *Color (upper surface).*—62C to 65B.
- *Color (under surface).*—65C.
- *Shape.*—Straight, oblong, slightly ribbed.

C. Corolla of disc florets:
- *Color (mature).*—14A.
- *Color (immature).*—144B.

D. Reproductive organs:
- *Androecium.*—Present on disc florets only; no pollen.
- *Gynoecium.*—Present on both ray and disc florets.

PLANT

A. General appearance:
- *Height.*—86 to 94 cm when grown in Salinas with 14 to 18 long days prior to start of short days; height is 104 to 112 cm when grown in Bogota with 21 long days prior to start of short days.

B. Foliage:
- *Color (upper surface).*—147A.
- *Color (under surface).*—147B.
- *Shape.*—Deeply lobed, strongly serrated.

What is claimed is:

1. A new and distinct Chrysanthemum plant named Pink Cinderella, as described and illustrated.

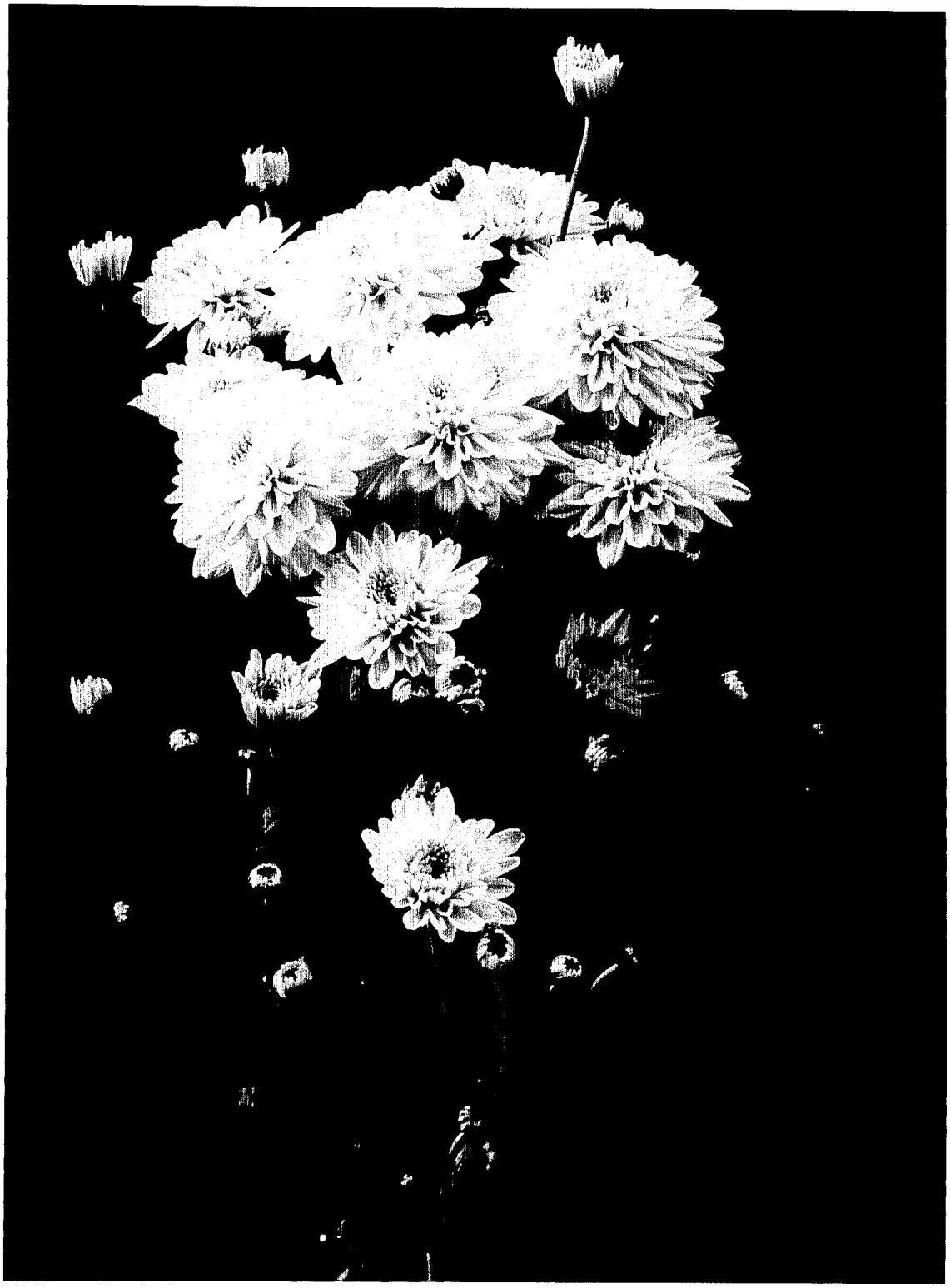

* * * * *